US008394389B2

(12) United States Patent
Lighter et al.

(10) Patent No.: US 8,394,389 B2
(45) Date of Patent: Mar. 12, 2013

(54) TUBERCULOSIS VACCINE AND METHOD OF USING SAME

(75) Inventors: Jennifer Lighter, New York, NY (US); Jason Fisher, New York, NY (US)

(73) Assignee: Mico Bio, Inc., New York, NY (US)

( * ) Notice: Subject to any disclaimer, the term of this patent is extended or adjusted under 35 U.S.C. 154(b) by 95 days.

(21) Appl. No.: 12/595,006

(22) PCT Filed: Apr. 11, 2008

(86) PCT No.: PCT/US2008/060065
§ 371 (c)(1),
(2), (4) Date: Jan. 21, 2010

(87) PCT Pub. No.: WO2008/128065
PCT Pub. Date: Oct. 23, 2008

(65) Prior Publication Data
US 2010/0112007 A1    May 6, 2010

Related U.S. Application Data

(60) Provisional application No. 60/923,301, filed on Apr. 12, 2007.

(51) Int. Cl.
*A61K 39/04*     (2006.01)
*A61K 49/00*     (2006.01)
*A61K 39/02*     (2006.01)

(52) U.S. Cl. ..... 424/248.1; 424/9.1; 424/9.2; 424/234.1

(58) Field of Classification Search .................. 424/9.1, 424/9.2, 234.1, 248.1
See application file for complete search history.

(56) References Cited

U.S. PATENT DOCUMENTS 4,724,144 A * 2/1988 Rook et al. ................. 424/248.1

FOREIGN PATENT DOCUMENTS

WO        WO00/47225     *   8/2000
WO        WO-0047225 A2     8/2000

OTHER PUBLICATIONS

Haile, M., et al. Vaccine, vol. 22, pp. 1498-1508, 2004.*
Nishihara, H., et al. American Review of Respiratory Disease, vol. 88, No. 6, p. 182-186, 1963.*
Carpenter, C.M., et al. American Review of Tuberculosis, vol. 79, No. 3, pp. 374-377, 1959.*
Giri, P.K., et al. FEMS Immunology and Medical Microbiology, vol. 45, No. 1, pp. 87-93, 2005.*
Haile et al., "Immunization with heat-killed *Mycobacterium bovis* bacille Calmette-Guerin (BCG) in Eurocine(TM) L3 adjuvant protects against tuberculosis", Vaccine, 22:1498-1508 (2004).
Falero-Diaz et al., "Intranasal vaccination of mice against infection with *Mycobacterium tuberculosis*", Vaccine, 18:3223-3229 (2000).
Chen et al., "Single intranasal Mucosal *Myobacterium bovis* BCG Vaccination Confers IMproved Protection Compared to Subcutaneous Vaccination against Pulmonary Tuberculosis", Infection and Immunity, 72(1):238-246 (2004).
De La Barrere et al., "IL-10 down-regulates costimulatory molecules on *Mycobcaterium tuberculosis*-pulsed macrophages and impairs the lytic activity of CD4 and CD8 CTL in tuberculosis patients", Clin. Exp. Immunol., 138:128-138 (2004).
Zammit et al., "Residual Antigen Presentation after Influenza Virus Infection Affects CD8 T Cell Activation and Migration", Immunity, 24:439-449 (2006).
Bahr, G.M. et al., Improved immunotherapy for pulmonary tuberculosis with *Mycobacterium vaccae*. Tubercle 71:259-266 (1990).
Brennan, M.J. et al., Tuberculosis vaccine development: research, regulatory and clinical strategies. *Expert Opin. Biol. Ther.* 4(9): 1493-1504 (2004).
Pozniak, A.L. et al., A tenative introduction of immunotherapy into the treatment of tuberculosis. *Bulletin of the International Union Against Tuberculosis and Lung Disease* 62(4) 39-40 (1987).
Rook, G.A.W., et al., Cytokines and the Koch phenomenon. *Tubercle* 72: 13-20 (1991).
Stanford, J.L., et al., Immunotherapy with *Mycobacterium vaccae* as an adjunct to chemotherapy in the treatment of pulmonary tuberculosis. *Tubercle* 71:87-93 (1990).
Stanford, J.L., Koch's phenomenon: can it be corrected? *Tubercle* 72: 241-249 (1991).
Stanford, J., et al., Immunotherapy with *Mycobacterium vaccae* in the treatment of tuberculosis. *Frontiers in Bioscience* 9: 1701-1719 (2004).
J.L. Stanford and A.W. Rook, "Immunotherapy for mycobacterial diseases", in Mycobacteria: molecular biology and virulence (1999), Ratledge, C. and Dale, J., ed., Blackwell Science Ltd., Oxford, Ch. 16.
Attiyah et al., Clin. Exp. Immunol. (1992) 88:537-542.
Bahr et al., Tubercle (1986) 67:205-218.
Bothamley et al., Tubercle (1991) 72:7-11.
Cardona et al., Arch Bronconeumol, (2006) 42(1):25-32.
Cardona et al., Scand. J. Immunol. (2001) 53:65-71.
Cardona, Vaccine, (2005) 23:1393-1398.
Cardona, Tuberculosis (2006) 86:273-289.
Domingo, Scand J. Immunol.(2009) 69:6, 500-507.
Dubos et al., J. Exp. Med. (1953) 97:221-231.
Gil et al., Microbes and Infection (2006) 8:628-636.
Haile, Tuberculosis, (2005) 85:107-114.
Ibanga et al., Lancet Infect Dis, (2006) 6:522-528.
Kanai J. Med. Sci. Biol. (1967) 20:21-72.
Kaufmann et al., Lancet, (2010) 375:2110-2019.
Lurie, J. Exp. Med. (1932) 55:31-58.
Nishihara et al. Am. Rev. Respir Dis, (1963) 88:827-832.
Rook et al., Tuberculosis, (1996) 240-258.
Rook et al., Parasite Immunology (1979) 1:111-123.
Rook et al., Eur. Respir. J. (2001) 17:537-557.
Svenson et al., Human Vaccines, (2010) 6:309-317.

* cited by examiner

*Primary Examiner* — Rodney P. Swartz
(74) *Attorney, Agent, or Firm* — Mintz Levin Cohn Ferris Glovsky and Popeo, P.C.; Muriel Liberto, Esq.

(57) ABSTRACT

Provided is a pharmaceutical composition that includes one or more inactivated *Mycobacterium* spp., which are preferably inactivated using gamma irradiation, and which is then formulated for mucosal or pulmonary delivery to a subject. The pharmaceutical compositions are useful for preventing or treating *mycobacterium*-associated infections in a subject, including a human subject.

11 Claims, No Drawings

TUBERCULOSIS VACCINE AND METHOD OF USING SAME

RELATED APPLICATIONS

This application is a national stage application, filed under 35 U.S.C. §371, of International Application No. PCT/US2008/060065, filed on Apr. 11, 2008, which claims the benefit of U.S. patent application Ser. No. 60/923,301, filed on Apr. 12, 2007.

FIELD OF THE INVENTION

The invention relates to a vaccine against tuberculosis and more particularly to a vaccine using inactivated *Mycobacterium* spp. formulated for pulmonary and mucosal delivery.

BACKGROUND OF THE INVENTION

*Mycobacterium tuberculosis* (*M. tb*) infects one third of the world's human population[1]. The common tuberculosis (TB) vaccine known as the BCG vaccine is given to neonates in developing countries. While this vaccine protects against meningeal and disseminated TB in children, it fails to adequately protect the establishment of latent TB or reactivation of pulmonary disease in adult life[2]. Moreover, BCG effectiveness is reported to decline over a period of 10-15 years[3]. The most common type of tuberculosis disease is pulmonary and transmission occurs via aerosol droplets expressed during coughing. Thus, despite the high prevalence of BCG vaccination, the disease burden has not decreased. There is now evidence to support that *M. tb* mycobacterial lineages may have adapted to mutations in antigens common to both *M. tb* and BCG[4,5]. Moreover, recent studies suggest that BCG delivered parenterally may fail to induce T-cell immune responses in the lung mucosa, which may be critical for protection against pulmonary disease[6,7]. Given these reasons, a new vaccine is imperative to decrease the prevalence of TB throughout the World.

SUMMARY OF THE INVENTION

The invention provides a vaccine for preventing and/or treating tuberculosis. The invention can be utilized with a number of vaccination strategies: prophylactically-given prior to infection to prevent infection, post-exposure to eliminate or contain latent TB and prevent reactivation. It can either be used to replace BCG and/or as a booster to BCG in patients who have already received BCG or another subunit TB immunostimulant.

In one aspect, the invention provides a pharmaceutical composition comprising an inactivated *Mycobacterium* spp., wherein the composition is formulated for intranasal, mucosal or intrapulmonary delivery to a mammalian host, and wherein the composition comprises an immunologically protective dose when delivered to the host.

Suitable *Mycobacterium* spp. include, e.g., *M. tuberculosis, M. marinum, M. bovis, M. africanum*, or *M. microtti*. In some embodiments, the inactivated *Mycobacterium* spp. cells are killed cells or cell lysates.

In some embodiments, at least 90% of the *Mycobacterium* spp. cells are inactivated, e.g., 95%, 98%, 99%, or 100% of the *Mycobacterium* spp. cells. When the subject is a human, 100% of the *Mycobacterium* spp. cells are preferably inactivated.

In some embodiments, the *Mycobacterium* spp. is inactivated with irradiation. Preferably irradiation is with gamma irradiation.

In other embodiments, the *Mycobacterium* spp. is inactivated with formalin or heat.

In some embodiments, the *Mycobacterium* spp. is inactivated with osmotic pressure via salts or drying process.

The pharmaceutical composition may optionally include an adjuvant to enhance an immune response in the host.

The pharmaceutical composition may optionally include a pharmaceutically acceptable carrier, or be provided lyophilized.

In some embodiments, the pharmaceutical composition is formulated for intranasal delivery to the host.

In addition, the pharmaceutical composition is provided as an aerosol or spray package.

In one embodiment, the invention provides a pharmaceutical composition that includes a gamma-irradiated *Mycobacterium* spp. that is formulated for intranasal or intrapulmonary delivery to a mammalian host and which confers an immunologically protective dose when delivered to the host, e.g., a human.

In another aspect, the invention provides a method of vaccinating a mammal against TB. The method includes administering to the mammal a composition comprising inactivated *Mycobacterium* spp., wherein the vaccination of the mammal is intranasal or intrapulmonary, and wherein the composition comprises an immunologically protective dose when delivered to the host.

In another aspect, the invention provides an immunostimulant that facilitates delivery of another antigen.

In one aspect, the invention provides a pharmaceutical composition comprising an inactivated *Mycobacterium* spp., wherein the composition is formulated for intranasal, mucosal or intrapulmonary delivery to a mammalian host, and wherein the composition comprises an immunologically protective dose when delivered to the host.

Suitable *Mycobacterium* spp. for use in the method include, e.g., *M. tuberculosis, M. marinum, M. bovis, M. africanum*, or *M. microtti*. In some embodiments, the inactivated *Mycobacterium* spp. cells are killed cells or cell lysates. In some embodiments, at least 90% of the *Mycobacterium* spp. cells are inactivated, e.g., 95%, 98%, 99%, or 100% of the *Mycobacterium* spp. cells. When the subject is a human, 100% of the *Mycobacterium* spp. cells are preferably inactivated.

In some embodiments, the *Mycobacterium* spp. for use in the method is inactivated with irradiation. Preferably irradiation is with gamma irradiation. In other embodiments, the *Mycobacterium* spp. is inactivated with formalin or heat.

The pharmaceutical composition for use in the method may optionally include an adjuvant to enhance a protective immune response in the host.

The pharmaceutical composition for use in the method may optionally include a pharmaceutically acceptable carrier, or be provided lyophilized.

In some embodiments, the pharmaceutical composition for use in the method is formulated for intranasal delivery to the host.

In addition, the pharmaceutical composition for use in the method is provided as an aerosol or spray package.

In some embodiments, the pharmaceutical composition is delivered through a device configured for nasal or pulmonary delivery.

In a still further aspect, the invention provides a method for preparing a vaccine for treating *Mycobacterium* infection, comprising formulating an immunologically protective dose of an inactivated *Mycobacterium* spp. for intranasal or pulmonary delivery to a mammalian host.

In some embodiments, the method includes testing the vaccine in a non-human animal model of tuberculosis. The animal model can be, e.g., a mouse, guinea pig, rabbit, bovine, or non-human primate.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

A vaccine according to the invention is prepared using one or more inactivated *Mycobacterium* spp. that is then formulated for pulmonary and mucosal delivery to a subject. The inactivated *mycobacterium*, when delivered to the lung or mucosal/nasal mucosa of a subject is postulated to elicit a much stronger immune response than has been observed with previously described Tb vaccines.

Research in an influenza murine model suggests that pulmonary immune cells remain localized and only a few B cells and T cells migrate systemically.[8,9] The research shows that key influenza-specific CD8-T cells can remain locked within a semi-isolated circuit within the chest, barely reaching the bloodstream or the peripheral lymphoid tissue but instead cycling between the respiratory mucosa and the local lymph nodes. Zammit et al suggest that one reason may be the special anatomy of the lung lymphatic drainage[8]. Cells entering the thoracic duct from the local pulmonary nodes are fed to the lung in the pulmonary arterial blood. Some may pass through to the systemic circulation, but activated cells tend to adhere to the vascular endothelium and move back into the lung, thus keeping cells at the site of infection. From here the cells again move to the local nodes where they re-encounter antigen. Indeed, it has been found in the murine TB model that antigen specific memory T-cells preferentially home back to the site of vaccination and that the location of T cells in the airway at the time of infection is of importance[10-11].

Applying these findings to the instant invention, then, for a TB vaccine to be successful in evoking a protective immune response in the pulmonary and respiratory mucosal system, it preferably directly stimulates the antigen-presenting cells in the respiratory epithelium. The invention accomplishes this by delivering irradiated *mycobacterium* directly to the pulmonary and mucosal interface.

One study published in 1968 reported no adverse effects when aerogenic BCG was given to 439 children[12]. In experimental animal species, aerosol or intra-tracheal delivery of BCG varied in efficacy from superior protection than parenteral inoculation in primates[13], cattle[14] guinea pigs[15], and mice[16,17,18,19] to no apparent advantage over the subcutaneous route in other studies[20]. Other studies showed immune response was dependent on initial BCG inoculum dose[12,21].

Recently, several research groups have published data on using mucosal *M. tb* subunit vaccines as booster when administered weeks after primary immunization in the murine model. Goonetilleke et al findings support the importance of homing properties of T cells when exposed to recombinant modified vaccinia virus Ankara, expressing *Mycobacterium tuberculosis* Ag 85A. Intranasal boosting induced a five fold higher T cell response in the lungs than parenteral BCG thereby providing support that T cells in the lungs are in some form compartmentalized[22]. Santosuosso et al showed that an intranasal adenoviral vector expressing Ag85A boosted primary CD4 and CD8 T-cell response in the airway lumen and enhanced protection against pulmonary *M. tuberculosis* challenge[23]. Other studies in mice using mycobacterial antigens (Ag 85A or Ag 85B-ESAT-6) in either recombinant bacterial/viral vectors or with proteins and adjuvants given mucosally as a booster have shown protective immunity when compared to standard parenteral BCG when challenged with live *M. tb*[24,25,26]. All of these studies showed statistically fewer colony forming units of *mycobacteria* in the lungs and spleen after the mucosal subunit vaccine boost when compared to BCG alone.

The adaptive immune response to live *M. tuberculosis* infection is delayed compared to other infections and this allows the bacilli population in the lungs to markedly increase during the preimmune phase of the infection[27]. By using dead baciili in an aerosolized vaccine formulation there is no multiplying *mycobacteria* and the immune response would have adequate time to respond to the antigens on the cell wall of the bacteria. In addition, over thousands of years through fitness challenges *M. tb* has found many ways to evade the innate immune response during initial antigen presentation[28,29,30,31]. Dead *mycobacteria* do not have the ability to produce enzymes that evoke ways to evade the human immune system and avoid successful antigen presentation.

One reason we believe this method of using killed whole *mycobacterium* has been overlooked in the past is due to studies performed by Robert Koch in the late 19$^{th}$ century[32]. Koch used a sterile filtrate from *M. tuberculosis* cultures as a therapeutic vaccine in subjects. This induced such a severe inflammatory immune response in some individual's with active disease, that some died. Known as the Koch phenomenon, this necrotic reaction appears to be due to overproduction of several pro-inflammatory cytokines but in particular TNF-$\alpha$[33]. This incident haunted vaccinologists for decades and we believe scientists have since overlooked the potential use of whole bacilli. Whole killed *mycobacterium* will be utilized in low enough quantities to avoid an overwhelming inflammatory reaction and yet still elicit a strong immunoprotective response In general, any type of inactivation procedure can be used as long as the treatment leaves the population of bacteria unable to produce a productive infection at the host, while at the same time preserving antigenic structures necessarily for eliciting a productive response to the corresponding disease-causing *mycobacterium*. The *mycobacterium* preparation is typically incapacitated. By "incapacitated" in the context of an incapacitated bacterial cell produced according to the invention, is meant that the bacterial cell is in a state of irreversible bacteriostasis. While the bacterium retains its structure—and thus retains, for example, the immunogenicity, antigenicity, and/or receptor-ligand interactions associated with a wild-type bacterium—it is not capable of replicating. In some embodiments, it is incapable of replication due to the presence of an infecting phage with in the bacterial cell.

A preferred type of inactivation is gamma-irradiation. Other types of inactivation known in the art include, e.g., other types of radiation (including ultra-violet irradiation), formalin treatment, and heat treatment. In some embodiments for non-human use, >70% of the cells are killed. In the embodiments for human use, 100% of the cells are killed.

While not wishing to be bound by theory, it is postulated that gamma-irradiated *Mycobacterium* are especially suitable for use in the compositions and methods of the invention. Gamma-irradiated bacteria are commonly used in the laboratory because they are considered safe and do not replicate. In many trials, they have nevertheless been shown to elicit an immunoprotective response, including responses elicited by antigens on the bacilli wall[34,35,36]. In addition, gamma irradiated *mycobacterium* undergo apoptosis and become engulfed by dendritic cells. Dendritic cells present the *mycobacterium* antigens to T-cells, which activate CD4 Th1 and CD8 cytotoxic cells. Gamma-irradiated *M. tb* can also induce nitric oxide release[34] and can elicit similar Th2 responses to live *M. tb*[35]. In 1963, Nishihara et al intradermally injected gamma-irradiated *M. tb* into mice and found it was equally as protective as BCG injected intradermally against aerosol challenge with *M. tb*[37].

Delivery of the irradiated bacteria or the bacterial antigens to the lung and mucosal border is believed to facilitate an effective immune response in the host. Upon delivery to the nasal mucosa or alveolar passages, the bacteria or bacteria antigens are detected by antigen presenting cells, specifically dendritic cells at the alveoli/interstitial space of the lung. These dendritic cells then migrate to the regions enriched in naïve CD4+ and CD8+ T-cells and which constitute the paracortical zone of the regional lymph nodes of the lung. These T cells are activated by the dead bacilli's antigens. The dead mycobacteria will become phagocytosed by macrophages.

In general, any *Mycobacterium* species or strain that is a member of the *M. tuberculosis* complex can be used in the composition and methods of the invention. Suitable species, *Mycobacterium* which are members of the *M. tb* complex include, e.g, *Mycobacterium bovis, Mycobacterium africanum, Mycobacterium microtti*, and *Mycobacterium tuberculosis. Mycobacterium* that are genetically similar include *Mycobacterium canettii* and *Mycobacterium marinum*. The particular species or combination of species is selected for the corresponding host species and type *Mycobacterium* associated disease to be treated. Other *Mycobacteria* that cause disease in humans include, e.g., *Mycobacterium avium intracellulare, Mycobacterium leprae, Mycobacterium lepraemurium, Mycobacteria paratuberculosis, Mycobacterium ulcerans, Mycobacterium smegmatis, Mycobacterium xenopi, Mycobacterium chelonei, Mycobacterium fortuitum, Mycobacterium farcinogenes, Mycobacterium flavum, Mycobacterium haemophilum, Mycobacterium kansasii, Mycobacterium phlei, Mycobacterium scrofulaceum, Mycobacterium senegalense, Mycobacterium simiae, Mycobacterium thermoresistible*, and *Mycobacterium xenopi*.

The *mycobacterium* to be used in the pharmaceutical composition can include whole cells or portions of cells, e.g., cell lysates. For example, suitable components include a gamma irradiated whole cell lysate, gamma irradiated culture filtrate proteins, gamma irradiated cell wall fraction, gamma irradiated cell membrane fraction, gamma irradiated cytosol fraction, gamma irradiated soluble cell wall proteins, and gamma irradiated soluble protein pool.

Preparing Pharmaceutical Compositions

The killed cells are prepared for administration to a host by combining inactivated cells or cell lysates with a pharmaceutically acceptable carrier to form a pharmaceutical composition. The carrier can be, e.g., such as physiological saline, mineral oil, vegetable oils, aqueous sodium carboxymethyl cellulose, or aqueous polyvinylpyrrolidone. In some embodiments, the carrier is sufficiently pure to be administered therapeutically to a human subject. Those of relevant skill in the art are well able to prepare suitable solutions using, for example, isotonic vehicles such as Sodium Chloride Injection, Ringer's Injection, or Lactated Ringer's Injection. Preservatives, stabilizers, buffers, antioxidants and/or other additives may be included, as required.

A skilled person in the field familiar with the protocols, formulations, dosages and clinical practice associated with, e.g., the administration of *M. bovis* BCG can in addition readily adapt these protocols for use with pharmaceutical compositions of the present invention. The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations. Thus, the vaccine may be administered in a single dose or in a plurality of doses. In one embodiment, the vaccine may be administered in two doses about 1-12 months apart. The subject may be vaccinated at any time, although it is preferred to administer the vaccine shortly (optimally about 10 days to two weeks) before periods of anticipated stress, such as during shipping or other handling. It is also envisioned that the vaccine may be administered to pregnant animals prior to birth to increase production of hyper immune colostrum.

A composition may be administered alone or in combination with other treatments or standard BCG vaccine, either simultaneously or sequentially dependent upon the condition to be treated. The composition can be administered after vaccination with BCG and therefore act as a boosting tuberculosis vaccine. Moreover, it may be given after an initial subcutaneous inoculation of the whole killed bacilli followed by an intranasal or mucosal boost.

The killed cells may be incorporated into microparticles or microcapsules to prolong the exposure of the antigenic material to the subject animal and hence protect the animal against infection for long periods of time. The microparticles and capsules may be formed from a variety of well-known inert, biocompatible matrix materials using techniques conventional in the art. Suitable matrix materials include, e.g., natural or synthetic polymers such as alginates, poly(lactic acid), poly(lactic/glycolic acid), poly(caprolactone), polycarbonates, polyamides, polyanhydrides, polyortho esters, polyacetals, polycyanoacrylates, polyurethanes, ethytlene-vinyl acetate copolymers, polystyrenes, polyvinyl chloride, polyvinyl fluoride, poly(vinyl imidazole), chlorosulphonated polyolefins, polyethylene oxide, and particularly agar and polyacrylates. Examples of techniques for incorporation of materials into microparticles or encapsulation which may be used herein are described by Sparks[38], Kydonius[39], and El-Nokaly[40] the contents of each of which are incorporated by reference herein.

The inactivated *mycobacterium* may be contained in small particles suspended in the water or saline. The vaccine formulations may also contain optional adjuvants, antibacterial agents or other pharmaceutically active agents as are conventional in the art. Adjuvants may include but are not limited to salts, emulsions (including oil/water compositions), saponins, liposomal formulations, virus particles, polypeptides, pathogen-associated molecular patterns (PAMPS), nucleic acid-based compounds or other formulations utilizing certain atigens. Suitable adjuvants include, e.g., vegetable oils, alum, Freund's incomplete adjuvant, or Freund's incomplete adjuvant, with oils and Freund's incomplete adjuvant being particularly preferred. Other adjuvants include agents such as aluminum hydroxide or phosphate (alum), immune-stimulating complexes (ISCOMs), synthetic polymers of sugars (CARBOPOL®), aggregation of the protein in the vaccine by heat treatment, aggregation by reactivating with pepsin treated (Fab) antibodies to albumin, mixture with baterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

The inactivated *mycobacterium* may be contained in a mucosal bacterial toxin adjuvant such as the *Escherichia coli* labile toxin (LT) and cholera toxin (CT) or in CpG oligodeoxynucleotide (CpG ODN)[41]. Another possible mucosal adjuvant Monophosphoryl lipid A (MPL), a derivative and less toxic form of LPS, when combined with liposomes was found to induce mucosal immunoprotective responses[42]. One new adjuvant designed for nasal vaccination, Eurocine L3™, has been shown to induce long-lasting immunity against TB in experimental animal models after intranasal administration[43—45]. The adjuvant technology consists of a non-toxic pharmaceutical formulation based on a combination of endogenous and pharmaceutically accepted lipids. The vaccine may optionally include additional immune modulating substances such as cytokines or synthetic IFN-γ inducers such as poly I:C alone or in combination with the above-mentioned adjuvants.

Still other adjuvants include microparticles or beads of biocompatible matrix materials. The microparticles may be composed of any biocompatible matrix materials as are conventional in the art, including but not limited to, agar and polyacrylates. The practitioner skilled in the art will recognize that other carriers or adjuvants may be used as well. For example, Chitosan or any bioadhesive delivery system which may be used are described by Webb and Winkelstein[46] the contents of which are incorporated by reference herein.

The pharmaceutical composition containing the inactivated *mycobacterium* is preferably formulated for intranasal or intrapulmonary delivery using methods known in the art. The formulation of the irradiated *mycobacterium* combined with the adjuvant is preferably selected to minimize side effects, such as inflammation, associated with vaccination or may improve the formulation's stability. The adjuvant may also have a role as an immunostimulant or as a depot.

In some embodiments, the inactivated *mycobacterium* are delivered by the refinement of a nebulizer or via three types of compact portable devices, the metered-dose inhaler (MDI) and the dry powder inhaler (DPI). Intranasal delivery can occur via the nasal spray, dropper or nasal metered drug delivery device. The inactive *mycobacterium* may be delivered via a metered dose inhaler. Typically, only 10-20% of the emitted dose is deposited in the lung. The high velocity and large particle size of the spray causes approximately 50-80% of the drug aerosol to impact in the oropharyngeal region.

The *mycobacterium* may be contained in a dry powder formulation such as but not limited to a sugar carrier system. The Sugar Carrier System could include lactose, mannitol, and/or glucose. Lactose, mannitol, and glucose are all approved by the FDA as carriers. There are also larger sugar particles such as lactose monohydrate—typically 50-100 micrometers in diameter, which remain in the naso-oropharynx but allows the inactivated bacilli to travel through the respiratory tree into the alveoli.[47]

If desired, the *mycobacterium* may be contained in a liposomal formulation. Liposomes, like other inhaled particles reaching the alveoli, are cleared by macrophages. The processing, uptake and recycling of liposomal phospholipids occurs through the same mechanism as endogenous surfactant via the alveolar type II cells.

A pharmaceutical composition containing the irradiated *mycobacterium* described above is administered to a suitable individual for preventing or treating tuberculosis. Reference herein to "tuberculosis" includes reference to pulmonary and extra-pulmonary tuberculi. The terms "individual," "subject," "host," and "patient," are used interchangeably herein and refer to any subject having a bacterial infection amenable to treatment using the therapeutic vaccine of the invention, and for whom treatment or therapy is desired. The pharmaceutical composition can be prepared for any mammalian host that is susceptible to infection by *mycobacterium*. Suitable mammalian hosts include, e.g., farm animals such as swine and bovine The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, particularly a mammalian subject, more particularly a human, and includes: (a) preventing the disease or symptom from occurring in a subject which may be predisposed to the disease or symptom but has not yet been diagnosed as having it; (b) inhibiting the disease symptom, i.e., arresting its development; or relieving the disease symptom, i.e., causing regression of the disease or symptom (c) preventing reactivation of the disease in latent TB, i.e. preventing the bacilli from transitioning from a dormant to growth phase. Thus, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical or veterinarian personnel.

The subject treated with the vaccine typically will have or will develop protective immunity to an infecting bacterium. The term "protective immunity" means that a vaccine, immunogenic composition or immunization schedule that is administered to a mammal induces an immune response that prevents, retards the development of, or reduces the severity of a disease that is caused by a pathogenic bacterium or diminishes or altogether eliminates the symptoms of the disease. By "infecting bacterium" is meant a bacterium that has established infection in the host, and which may be associated with a disease or undesirable symptom as a result. Generally, infecting bacteria are pathogenic bacteria.

The phrase "in a sufficient amount to elicit an immune response" means that there is a detectable difference between an immune response indicator measured before and after administration of a particular vaccine preparation or immunogenic composition. Animals given the vaccine trial will be tested against animals give intradermal BCG (as the gold standard). Several weeks after the last vaccination, animals will be challenged with aerosol virulent *M. tb*. The clinical and molecular immune response will be evaluated several weeks after challenge with virulent *M. tb*.

Screening and Developing Tuberculosis Vaccines

A test vaccine can be screened or optimized by subjecting a population of *mycobacterium* cells, or fractions thereof (as described above) to various inactivation regimens, preparing a candidate pharmaceutical composition containing the treated cells or cell fractions and testing the ability of the treated composition using the methods described above to elicit an immune response and/or mount an effective challenge to *mycobacterium* infection in a host.

The terms "immunogenic bacterial composition", "immunogenic composition", and "vaccine" are used interchangeably herein to mean a preparation capable of eliciting a cellular and/or humoral immune response in a subject when administered in a sufficient amount to elicit an immune response to epitopes present in said preparation.

Immunopotency of the antigenic molecule expressed by the *mycobacterium* cell or extract preparation, can be determined by monitoring the immune response of test animals following immunization with the bacteria expressing the recombinant antigen. Test animals may include mice, guinea pigs, rabbits, bovine, non-human primates, and eventually human subjects.

The immune response of the test subject can additionally be analyzed by various approaches such as: (a) T-cell associate cytokine production (b) plasma cytokine production (c) T cell proliferation, cytoxicity, cytokine profiles (d) T cell antigen repertoire (e) T cell regulatory profiles (f) mRNA profiles (g) innate immunity profiles (h) antibody profiles (i) genetics and (j) protection from disease and/or mitigation of infectious symptoms in immunized animals.

REFERENCES

1. World Health Organization. Global Tuberculosis Control: Surveillance, Planning Financing. WHO report 2002. Geneva, Switzerland: WHO, 2002.
2. Fine, P E. Variation in protection by BCG: implications of and for heterologous immunity. Lancet 1995; 346:1339-1345
3. World Health Organization. 2001. WHO-vaccine preventable diseases: monitoring system. 2000 global summary. World Health Organization, Geneva Switzerland.
4. Behr M A, Wilson M A, Gill W P, Salamon H, Schoolnik G K, Rane S, et al. Comparative genomics of BCG vaccines by whole-genome DNA microarray. Science 1999; 284 (5419):1328-1334
5. Gagneux S, DeRiemer K, Van T, Kato-Maeda M, de Jong B C, Narayanan S, et al. Variable host-pathogen compatibility in *Mycobacterium tuberculosis*. Proc Natl Acad Sci USA. 2006; 103(8):2869-2873
6. Gallichan W S and Rosentahl K L. Long-lived cytotoxic T lymphocyte memory in mucosal tissues after mucosal but not systemic immunization. Journal of Experimental Medicine 1996; 184:1879
7. Belyakov I M Moss B, Strober W, Berzofsky J A. Mucosal vaccination overcomes the barrier to recombinant vaccinia immunization caused by preexisting poxvirus immunity. Processions for the National Academy of Science 1999; 96:4512
8. Zammit D J, Turner D L, Klonowski K D, Lefrancois L, Cauley L S. Residual Antigen Presentation after Influenza Virus Infection Affects CD8 T Cell Activation and Migration. Immunity. 2006; 24: 439-449.
9. Zammit D J, Cauley L S, Pham Q M, Lefrancois L. Dendritic Cells Maximize the Memory CD8 T Cell Response to Infection. Immunity. 2005; 22: 561-570.
10. Kamath, A. B., J. Woodworth, X. Xiong, C. Taylor, Y. Weng, S. M. Behar. 2004. Cytolytic CD8$^+$ T cells recognizing CFP10 are recruited to the lung after *Mycobacterium tuberculosis* infection. J. Exp. Med. 200: 1479-1489.
11. Santosuosso, M., X. Zhang, S. McCormick, J. Wang, M. Hitt, Z. Xing. 2005. Mechanisms of mucosal and parenteral tuberculosis vaccinations: adenoviral-based mucosal immunization preferentially elicits sustained accumulation of immune protective CD4 and CD8 T cells within the airway lumen. J. Immunol. 174: 7986-7994.
12. Rosenthal S R, McEnery J T, Raisys N. Aerogenic BCG Vaccination Against Tuberculosis in Animal and Human Subjects. The Journal of Asthma Research. 1968; 5: 3030-322.
13. Barclay W R, Busey W M, Dalgard D W, Good R C, Janicki B W, Kasik J E, Ribi E, Ulrich C E, Wolinsky E. Protection of Monkeys against Airborne Tuberculosis by Aerosol Vaccination and *Bacillus* Calmette-Guerin. American Review of Respiratory Disease. 1973; 107: 351-358.
14. Buddle B M, Keen D, Thomson A, Jowett G, McCarthy A R, Heslop J, De Lisle G W, Standford, J L, Aldwell F E. Protection of cattle from bovine tuberculosis by vaccination with BCG by the respiratory or subcutaneous route, but not by vaccination with killed *Mycobacterium vaccae*. Research in Veterinary Science. 1995; 59: 10-16.
15. Lagraderie M, Balazuc A M, Deriaud E, Leclerc C D, Gheorghiu M. Comparison of immune responses of mice immunized with five different *Mycobacterium bovix* BCG vaccine strains. Infection Immunity. 1996; 64 (1): 1-9.
16. Lefford M J. Immunization of Mice after Airborne Infection with Various Strains of BCG. American Review of Respiratory Disease. 1978; 117: 103-109
17. Falero-Diaz G, Challacombe S, Banerjee D, Douce G, Boyd A, Ivanyi J. Intranasal vaccination of mice against infection with *Mycobacterium tuberculosis*. Vaccine. 2000; 18 (28): 3223-3229.
18. Nuermberger E L, Yoshimatsu T, Tyagi S, Bishai W R, Grosset J H. Paucibacillary Tuberculosis in Mice after Prior Aerosol Immunization with *Mycobacterium bovis* BCG. Infection and Immunity. 2004; 72 (2): 1065-1071.
19. Giri P K, Verma I, Khuller G K. Protective efficacy of intranasal vaccination with *Mycobacterium bovis* BDG against airway *Mycobacterium tuberculosis* challenge in mice. 2006 Journal of Infection. 53:350-356.
20. Orme, I M and Collins F M. Aerogenic vaccination of mice with *Mycobacterium bovis* BCG. Tubercle 1986; 67:133-140
21. Middlebrook G. Immunological Aspects of Airborne Infection: Reactions to Inhaled Antigens. National Jewish Hospital Denver. Bact Review. 1961; 25: 331-346.
22. Goonetilleke N P, McShane H Hannan C M, Anderson R J, Brookes R H Hill A V S. Enhanced Immunogenicity and Protective Efficacy Against *Mycobacterium tuberculosis* of Baccille Calmette-Guerin Vaccine Using Mucosal Administration and Boosting with a Recombinant modified vaccinia virus Ankara. Journal of Immunology 2003; 171(3):1602-1609
23. Santosuosso M, McCormick S, Zhang X, Zganiacz A, Xing Z. Intranalsal boosting with an adenovirus-vectored vaccine markedly enhances protection by parenteral *Mycobacterium bovis* BCG immunization against pulmonary tuberculosis. Infection and Immunity 2006; 74(8):4634-4643

24. Dietrich J, Andersen C, Rappuoli R, Doherty T M, Jensen C G, Andersen P. Mucosal Administration of Ag85B-ESAT-6 Protects against infection with *Mycobacterium tuberculosis* and boosts prior *Bacillus* Calmette-Guerin Immunity. The Journal of Immunology 2006; 177:6353-6360
25. Xing Z, Lichty B D. Use of recombinant virus-vectored tuberculosis vaccines for there respiratory mucosal immunization. Tuberculosis 2006; 86:211-217
26. Gartner T, Baeten M, Otieno S, Revets H, Baetselier P D, Huygen K. Mucosal prime-boost vaccination for tuberculosis based on TLR triggering OprI lipoprotein from *Pseudomonas aeruginosa* fused to mycolyl-transferase Ag85A. Immunology Letters 2007; 111:26-35.
27. Wolf A J, Desvignes L, Linas B, Banaiee N, Tamura T, Takatsu K, Ernst J D J Exp Med. 2008 Jan. 21; 205(1):105-15. Epub 2007 Dec. 24
28. Gagliardi M C, Lemassu A, Teloni R, Mariotti S, Sargentini V, Pardini M, Daffé M, Nisini R. Cell wall-associated alpha-glucan is instrumental for *Mycobacterium tuberculosis* to block CD1 molecule expression and disable the function of dendritic cell derived from infected monocyte. Cell Microbiol. 2007 August; 9(8):2081-92. Epub 2007 Apr. 17.
29. Pai R K, Convery M, Hamilton T A, Boom W H, Harding C V. Inhibition of IFN-gamma-induced class II transactivator expression by a 19-kDa lipoprotein from *Mycobacterium tuberculosis*: a potential mechanism for immune evasion. J Immunol. 2003 Jul. 1; 171(1):175-84.
30. Schaible U E, Winau F, Sieling P A, Fischer K, Collins H L, Hagens K, et al. Apoptosis facilitates anitgen presentation to T lymphocytes through MHC-1 and CD1 in tuberculosis. Nature Medicine 2003; 9(8):1039-1046
31. Kaufman S H, Cole S T, Mizrahi V, Rubin E, Nathan C. *Mycobacterium tuberculosis* and thewith *M. tb* host response. Journal of Experimental Medicine 2005; 201 (11):1693-1697
32. Koch R. Classics in infectious diseases. The etiology of tuberculosis: Robert Koch, Berlin Germany, 1882> Review of Infectious Diseases (1982) 4(6):1270-1274
33. Rook G A, Stanford J L: The Koch phenomenon and the immunopathology of tuberculosis. Current Topics of Microbiology and Immunology (1996) 215: 239-262
34. Roy S, Sharma S, Sharma M, Aggarwal R, Bose M. Induction of nitric oxide release from the human alveolar epithelial cell line A549: an in vitro correlate of innate immune response to *Mycobacterium tuberculosis*. Immunology. 2004; 112: 471-480.
35. Pereira R M S, Calegari-Silva T C, Hernandez M O, Saliba A M, Redner P, Pessolani M C V, Sarno E N, Sampaio E P, Lopez U G. *Mycobacterium leprae* induces NF-kB-dependent transcription repression in human Schwann cells. Biochemical and Biophysical Research Communications. 2005; 335: 20-26.
36. Barrera S D L, Aleman M, Musella R, Schierloh P, Pasquinelli V, Garcia V, Abbate E Sasian MDC. IL-10 down-regulates costimulatory molecules on *Mycobacterium tuberculosis* pulsed macrophages and impairs the lytic activity of CD4 and CD8 CTL in tuberculosis patients. Clinical Exp Immunology. 2004; 138: 128-138.
37. Nirshihara H, Lawrence C A, Taplin G V, Carpenter C M. Immunogenicity of gamma-irradiated *Mycobacterium tuberculosis* H37Rv (GIV) in mice. The American Review of Respiratory Disease. 1963; 88: 827-832.
38. Kirk-Othmer Encyclopedia of Chemical Technology, third edition, John Wiley & Sons, New York, (1981) volume 15, pages 470-493
39. Controlled Release Technologies: Methods, Theories, and Applications, CRC Press, Cleveland, Ohio, 1980
40. Polymeric Delivery Systems, Properties and Applications, ACS Symposium Series 520, American Chemical Society, Washington, D.C., 1993
41. Freytag L C, Clements J D. Mucosal adjuvants. Vaccine 2005; 23(15): 1804-1813
42. Childers N K, Miller K L, Tong G, Llarena J C, Greenway T, Ulrich J T et al. Adjuvant activity of monophosphoryl lipid A for nasal and oral immunization with soluble or liposome-associated antigen. Infection and Immunity 2000; 68:5509-5516
43. M. Haile, B. Hamasur, T. Jaxmar, D. Gavier-Widen, M. A. Chambers and B. Sanchez et al., Nasal boost with adjuvanted heat-killed BCG or arabinomannan-protein conjugate improves primary BCG-induced protection in C57BL/6 mice, *Tuberculosis (Edinburgh)* 85 (2005), pp. 107-114.
44. M. Haile, U. Schroder, B. Hamasur, A. Pawlowski, T. Jaxmar and G. Kallenius et al., Immunization with heat-killed *Mycobacterium bovis* Bacille Calmette-Guerin (BCG) in Eurocine L3 adjuvant protects against tuberculosis, *Vaccine* 22 (2004), pp. 1498-1508
45. B. Hamasur, M. Haile, A. Pawlowski, U. Schroder, A. Williams and G. Hatch et al., *Mycobacterium tuberculosis* arabinomannan-protein conjugates protect against tuberculosis, *Vaccine* 21 (2003), pp. 4081-4093
46. Basic & Clinical Immunology, Stites et al. (ed.), fifth edition, Lange Medical Publications, Los Altos, Calif., 1984, pages 282-285
47. Labiris N R, Dolovich M B. Pulmonary drug delivery. Part II: The role of inhalant delivery devices and drug formulations in therapeutic effectiveness of aerosolized medications. British Journal of Clinical Pharmacology. 2003: 56; 600-612.

Additional embodiments are within the claims.

What is claimed is:

1. A pharmaceutical aerosol or spray composition comprising an immunologically protective dose of inactivated whole *Mycobacterium tuberculosis* (*M.tb*) and a carrier suitable for intranasal or intrapulmonary delivery, wherein the *M.tb* is inactivated by irradiation and wherein the immunologically protective dose of the inactivated whole *M.tb* is an amount from 0.10 to 50 micrograms.

2. The pharmaceutical composition of claim 1, wherein 90% of the *M.tb* are inactivated.

3. The pharmaceutical composition of claim 1, wherein 100% of the *M.tb* inactivated.

4. The pharmaceutical composition of claim 1, wherein said inactivation is by gamma irradiation.

5. The pharmaceutical composition of claim 1, further comprising *M.tb* cell lysates.

6. The pharmaceutical, composition of claim 1, further comprising an adjuvant, provided that the adjuvant does not comprise lipids.

7. The pharmaceutical composition of claim 1, wherein said composition is lyophilized.

8. A package comprising the pharmaceutical composition of claim 1.

9. A method of vaccinating a human against tuberculosis which comprises administering the composition of claim 1 to the human by an intranasal or intrapulmonary route.

10. The method of claim 9, wherein at least 90% of the *M.tb* are inactivated.

11. The pharmaceutical composition of claim 1, wherein the composition does not comprise an adjuvant.

* * * * *